(12) United States Patent
Stefanchik et al.

(10) Patent No.: US 8,828,046 B2
(45) Date of Patent: Sep. 9, 2014

(54) LAPAROSCOPIC DEVICE WITH DISTAL HANDLE

(75) Inventors: David Stefanchik, Morrow, OH (US); Omar J. Vakharia, Cincinnati, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 926 days.

(21) Appl. No.: 12/904,280

(22) Filed: Oct. 14, 2010

(65) Prior Publication Data

US 2012/0095298 A1    Apr. 19, 2012

(51) Int. Cl.
*A61B 17/28*    (2006.01)
*A61B 17/29*    (2006.01)
*A61B 17/00*    (2006.01)

(52) U.S. Cl.
CPC ..... *A61B 17/2909* (2013.01); *A61B 2017/2927* (2013.01); *A61B 2017/291* (2013.01); *A61B 2017/00738* (2013.01); *A61B 2017/2929* (2013.01); *A61B 2017/2902* (2013.01)
USPC ........................................................ 606/205

(58) Field of Classification Search
CPC .......................... A61B 17/0218; A61B 17/025
USPC ................. 600/118, 131, 137, 141, 142, 146; 606/1, 130, 167, 170, 174, 205–208
See application file for complete search history.

(56) References Cited

U.S. PATENT DOCUMENTS

| | | |
|---|---|---|
| 4,762,455 A | 8/1988 | Coughlan et al. |
| 5,330,502 A | 7/1994 | Hassler et al. |
| 5,697,939 A | 12/1997 | Kubota et al. |
| 5,702,408 A | 12/1997 | Wales et al. |
| 5,716,352 A * | 2/1998 | Viola et al. .......................... 606/1 |

(Continued)

FOREIGN PATENT DOCUMENTS

| | | |
|---|---|---|
| FR | 2845889 A1 | 4/2004 |
| GB | 2 421 912 A | 7/2006 |
| WO | 03/086219 A2 | 10/2003 |
| WO | 2009126955 A2 | 10/2009 |

OTHER PUBLICATIONS

International Search Report for Application No. PCT/US2011/055965, issued Jan. 19, 2012. (5 pages).

(Continued)

*Primary Examiner* — Ryan Severson
*Assistant Examiner* — Anh Dang
(74) *Attorney, Agent, or Firm* — Mintz Levin Cohn Ferris Glovsky and Popeo, P.C.

(57) ABSTRACT

Methods and devices are provided for controlling movement of an end effector assembly, and in particular for causing mimicking motion between a handle and an end effector assembly. In an exemplary embodiment, a surgical device is provided having a handle or actuator, an elongate shaft, and an end effector assembly coupled to a distal end of the elongate shaft. The handle or actuator is configured such that movement of the handle is mimicked, not mirrored, by the end effector assembly. The mimicking motion can be achieved using various techniques, but in an exemplary embodiment the handle is located distal to an input joint, and motion is transferred to the end effector assembly through an output joint at a distal end of the elongate shaft. The motion is preferably transferred using a mechanical transmission coupled between the input and output joints.

24 Claims, 10 Drawing Sheets

(56) References Cited

U.S. PATENT DOCUMENTS

| | | |
|---|---|---|
| 5,792,135 A | 8/1998 | Madhani et al. |
| 5,908,436 A | 6/1999 | Cuschieri et al. |
| 5,951,574 A | 9/1999 | Stefanchik et al. |
| 6,364,888 B1 | 4/2002 | Niemeyer et al. |
| 7,364,852 B2 * | 4/2008 | Rouleau et al. ............... 435/325 |
| 7,398,707 B2 | 7/2008 | Morley et al. |
| 2003/0109898 A1 | 6/2003 | Schwarz et al. |
| 2005/0033357 A1 | 2/2005 | Braun |
| 2006/0094932 A1 | 5/2006 | Goldfarb et al. |
| 2007/0221700 A1 | 9/2007 | Ortiz et al. |

OTHER PUBLICATIONS

FlexDex: A Minimally Invasive Surgical Tool with Enhanced Dexterity and Intuitive Control, Awtar et al., Journal Of Medical Devices, Sep. 2010, vol. 4.

Robot Technology, vol. 3A: Teleoperations and Robotics: Evolution and Development, pp. 67-93, 1986.

* cited by examiner

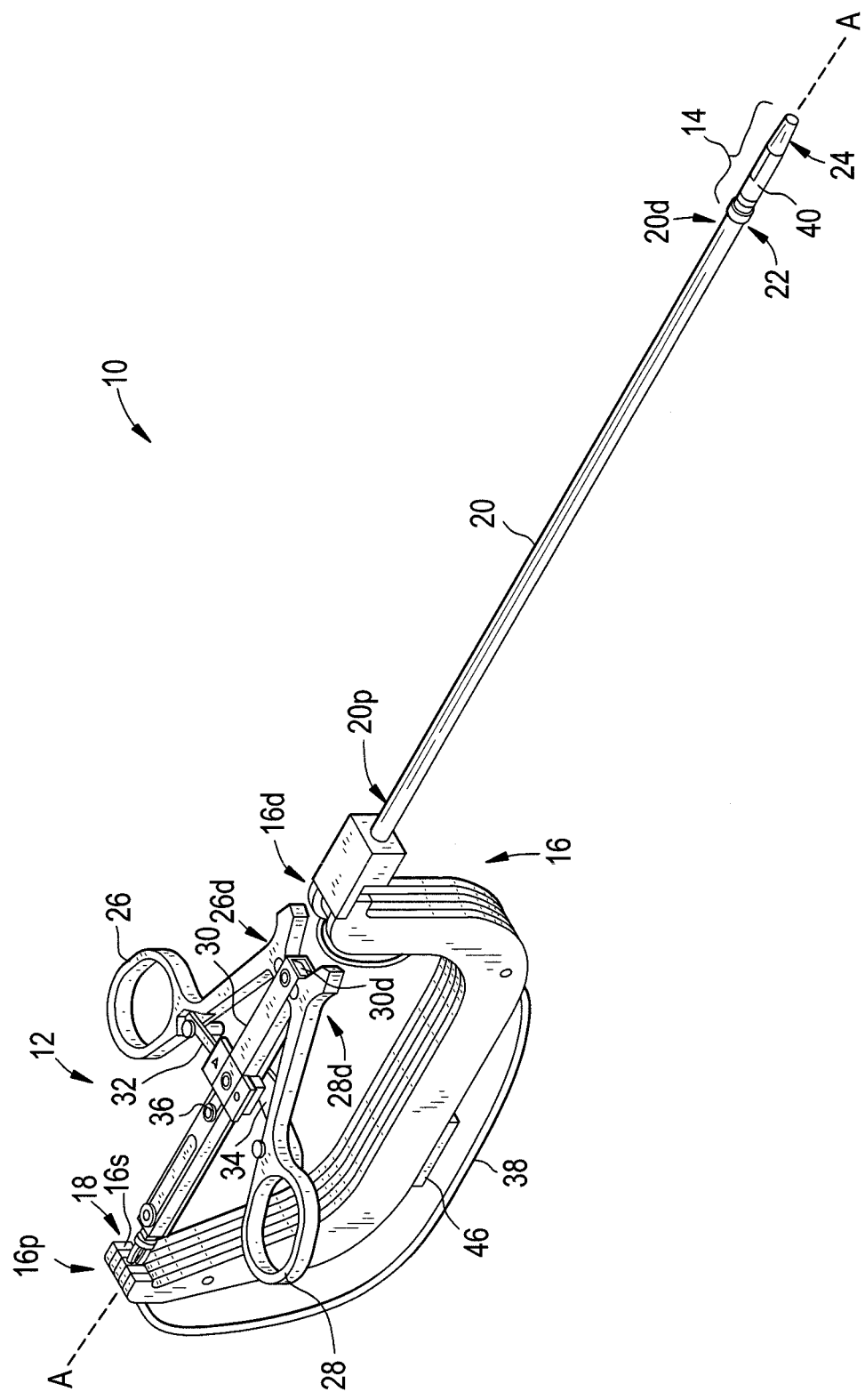

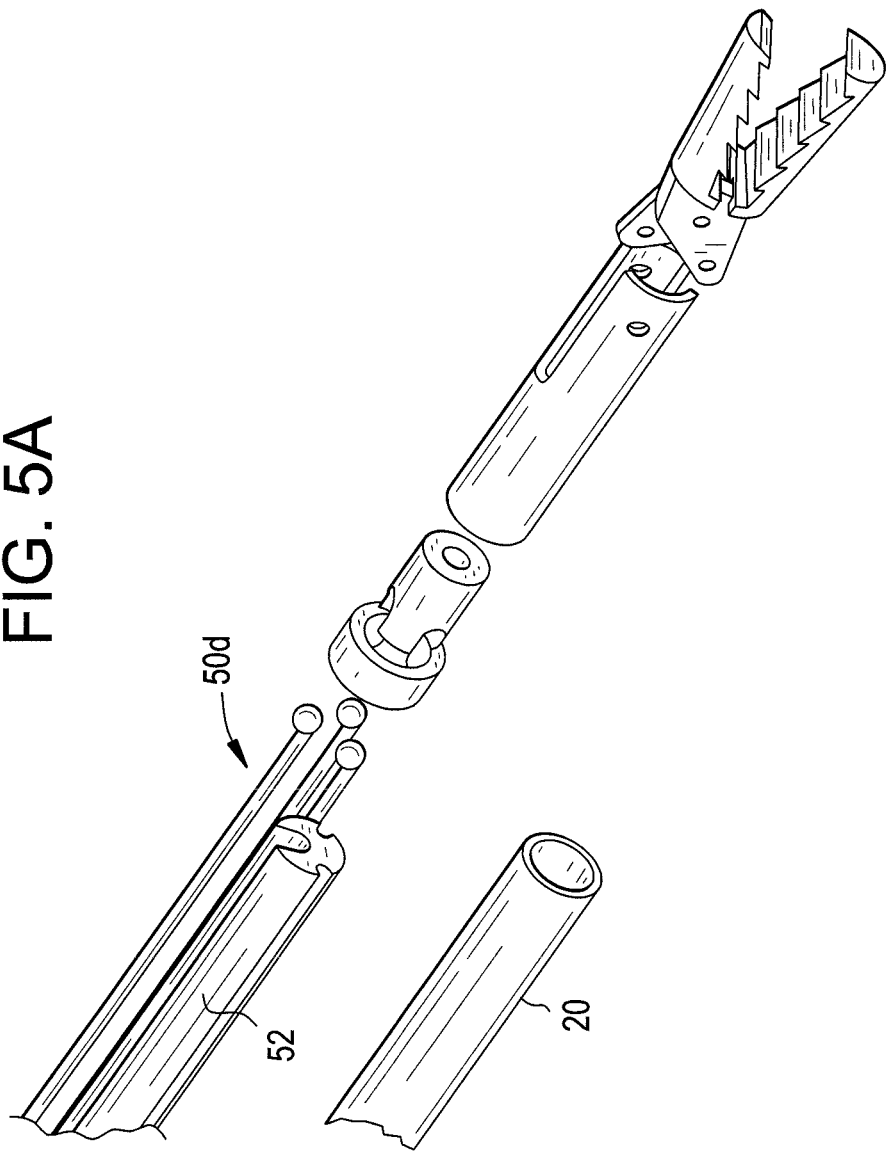

LAPAROSCOPIC DEVICE WITH DISTAL HANDLE

FIELD OF THE INVENTION

The present invention relates to methods and devices for controlling movement of an end effector assembly on a distal end of a surgical device, and in particular to methods and devices for causing mimicking motion between a handle and an end effector assembly.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Conventional MIS devices include a handle, an elongate shaft, and an end effector at the distal end for effecting tissue. Motion of the end effector is typically limited to four degrees of freedom (a degree of freedom is the direction in which the end effector can move). Furthermore, motion of the end effector mirrors motion of the handle, such that the operator needs to move the handle in a direction opposite to the desired direction of movement. Shear forces on MIS instruments can also be high, leading to increased operator fatigue.

Various robotic systems have been developed to assist in MIS procedures. Robotic systems can allow for more intuitive hand movements by maintaining both natural eye-hand axis. Robotic systems can also allow for more degrees of freedom in movement by including a "wrist" joint on the instrument, creating a more natural hand-like articulation. One drawback with robotic systems, however, is the loss of direct human contact with the tissue. There can be no true force feedback given to the surgeon. Another drawback is the high expense to manufacture such systems.

Accordingly, there remains a need for improved methods and devices for controlling movement of a working end of an endoscopic surgical device, and in particular to methods and devices that utilize a mechanical connection to provide for mimicking motion between a handle and an end effector.

SUMMARY OF THE INVENTION

The present invention generally provides surgical methods and devices in which motion of an actuator is mimicked, not mirrored, by motion of an end effector assembly. In one embodiment, a surgical device is provided having a frame with proximal and distal ends, an elongate shaft extending distally from the distal end of the frame, a mechanical transmission extending through the frame and elongate shaft between an input joint at the proximal end of the frame and an output joint at a distal end of the elongate shaft, an actuator extending distally from the proximal end of the frame and coupled to an input joint, and an end effector assembly positioned distal of the distal end of the elongate shaft and coupled to the output joint. Motion of the input joint is effective to cause correlating motion of the output joint such that movement of the actuator is mimicked by movement of the end effector assembly. In an exemplary embodiment, the actuator extends distally from a distal-facing surface of the proximal end of the frame.

The mechanical transmission can have a variety of configurations. In one embodiment, the mechanical transmission includes at least one transmission plate slidably disposed in the frame. The at least one transmission plate can be limited to movement along a fixed longitudinal axis. A proximal end of the at least one transmission plate can have be coupled to the input joint. The mechanical transmission can also include at least one transmission rod having a distal end connected to the output joint and a proximal end connected to the at least one transmission plate. In one embodiment, the output joint can be a ball-and-socket connection formed between the distal end of the mechanical transmission and the end effector assembly, and the input joint can be a ball-and-socket connection formed between the proximal end of the mechanical transmission and the actuator. In another embodiment, the proximal end of the at least one transmission plate can be coupled to the input joint by a coupler rod extending from the at least one transmission plate.

The mimicked motion between the actuator and the end effector assembly can include various types of movement. In one embodiment, the actuator and the end effector assembly can each have four or more degrees of freedom, which can include, for example, yawing, pitching, rolling, surging, heaving, and swaying. The movement of the end effector assembly can also be different in scale than the movement of the actuator. In one embodiment, the at least one transmission rod and the at least one transmission plate can be a first transmission rod connected to a first transmission plate, a second transmission rod connected to a second transmission plate, and a third transmission rod connected to a third transmission plate. Movement of the actuator can be effective to cause translation of the at least one transmission plate, and translation of the at least one transmission plate can be effective to cause translation of the at least one transmission rod coupled to the at least one transmission plate. In an exemplary embodiment, the first, second, and third transmission rods and plates can be configured to cause polyaxial articulation of the end effector assembly relative to the elongate shaft.

The surgical device can also have various other features. For example, in one embodiment the mechanical transmission can be configured to transfer surge of the actuator to the end effector assembly. This can be achieved by, for example, by having at least one of a proximal end of the elongate shaft being spaced a distance apart from the distal end of the frame, or a distal end of the elongate shaft being spaced a distance apart from the proximal end of the end effector assembly. The device can also include an actuation wire coupled between the actuator and the end effector assembly and configured to transfer opening and closing motion of the actuator to opening and closing motion of an end effector on the end effector assembly. In another embodiment, the frame can be C-shaped.

The actuator can also have various configurations. In an exemplary embodiment, the actuator is a hand-held actuator that is configured to be grasped by a user's hand without connecting to the user's forearm/wrist. The actuator can thus move independent of movement of the user's wrist joint. In one embodiment, the actuator can include one or more finger loops configured to receive human digits. The one or more finger loops can be pivotable relative to a handle. In an exemplary embodiment, the actuator is a scissor-type actuator, however other actuator configurations can be used.

In yet another embodiment, a surgical device is provided and includes a frame having proximal and distal ends, a hand-held actuator extending distally from a distal-facing surface of a proximal end of the frame and movable relative to the frame, an elongate shaft extending distally from the distal end of the frame and having an end effector assembly movably coupled to a distal end thereof, and a mechanical transmission extending through the frame and the elongate shaft. The mechanical transmission can be operably coupled between the actuator and the end effector assembly such that the mechanical transmission transfers motion of the actuator to cause mimicking motion of the end effector assembly. In one embodiment, the frame can be substantially C-shaped and the actuator can be positioned between proximal and distal ends of the frame. In another embodiment, the actuator and the end effector assembly can be coaxially aligned when the actuator and the end effector assembly are in a resting position. Alternatively, the actuator and the end effector assembly can be axially offset from one another when the actuator and the end effector assembly are in a resting position. The actuator can have various configurations, but preferably it is configured to be grasped by a user's hand without attaching to the user's wrist, as previously described above.

The mechanical transmission can have various configurations, but in one embodiment the mechanical transmission is in the form of at least one transmission plate slidably disposed within the frame and at least one transmission rod connected to the transmission plate and slidably disposed through the elongate shaft. The frame can be in the form of first and second stationary plates coupled to one another, and the at least one transmission plate can be disposed between the first and second stationary plates. In an exemplary embodiment, the mechanical transmission is in the form of a first transmission plate disposed in the frame and a first transmission rod connected to the first transmission plate and extending through the elongate shaft, a second transmission plate disposed in the frame and a second transmission rod connected to the second transmission plate and extending through the elongate shaft, and a third transmission plate disposed in the frame and a third transmission rod connected to the third transmission plate and extending through the elongate shaft. The first, second, and third transmission plates and rods can be effective to cause polyaxial articulation of the end effector assembly relative to a longitudinal axis of the elongate shaft. In further aspects, the surgical device can include an input joint disposed between the actuator and a proximal end of the mechanical transmission, and an output joint disposed between the a distal end of the mechanical transmission and the end effector assembly.

A surgical method is also provided and in one embodiment the method can include moving an actuator extending distally from a proximal end of a frame to transfer motion from an input joint coupled between the actuator a proximal end of the mechanical transmission, to an output joint coupled between a distal end of the mechanical transmission and an end effector assembly to thereby cause mimicking motion of the end effector assembly. The actuator can be moved, for example, by polyaxially articulating the actuator to cause correlating polyaxial articulation of the end effector assembly. In another embodiment, the mechanical transmission can be at least one transmission plate slidably coupled to the frame and at least one transmission rod coupled to the at least one transmission plate, and moving the actuator can causes at least one of the at least one transmission plates to slide relative to the frame which causes at least one of the transmission rods connected to the at least one transmission plate to translate longitudinally.

BRIEF DESCRIPTION OF THE DRAWINGS

The invention will be more fully understood from the following detailed description taken in conjunction with the accompanying drawings, in which:

FIG. 1A is a perspective view of one embodiment of a surgical device in accordance with the present invention;

FIG. 5A is an exploded perspective view of a distal portion of the device of FIG. 1A, showing an output joint and an end effector assembly;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for controlling movement of an end effector assembly, and in particular for causing mimicking motion between an actuator and an end effector assembly. In an exemplary embodiment, a surgical device is provided having a handle or actuator, an elongate shaft, and an end effector assembly coupled to a distal end of the elongate shaft. The handle or actuator is configured such that movement of the handle is mimicked, not mirrored, by the end effector assembly. In other words, the end effector assembly will move in the identical direction of movement of the actuator. The motion can, however, differ in scale. The mimicking motion can be achieved using various techniques, but in an exemplary embodiment the actuator is located distal to an input joint, and motion is transferred to the end effector assembly through an output joint at a distal end of the elongate shaft. The motion is preferably transferred using a mechanical transmission coupled between the input and output joints. A person skilled in the art will appreciate that the methods and devices disclosed herein can be used in connection with a variety of surgical procedures, including open, laparoscopic, and endoscopic procedures.

Figure 1B:
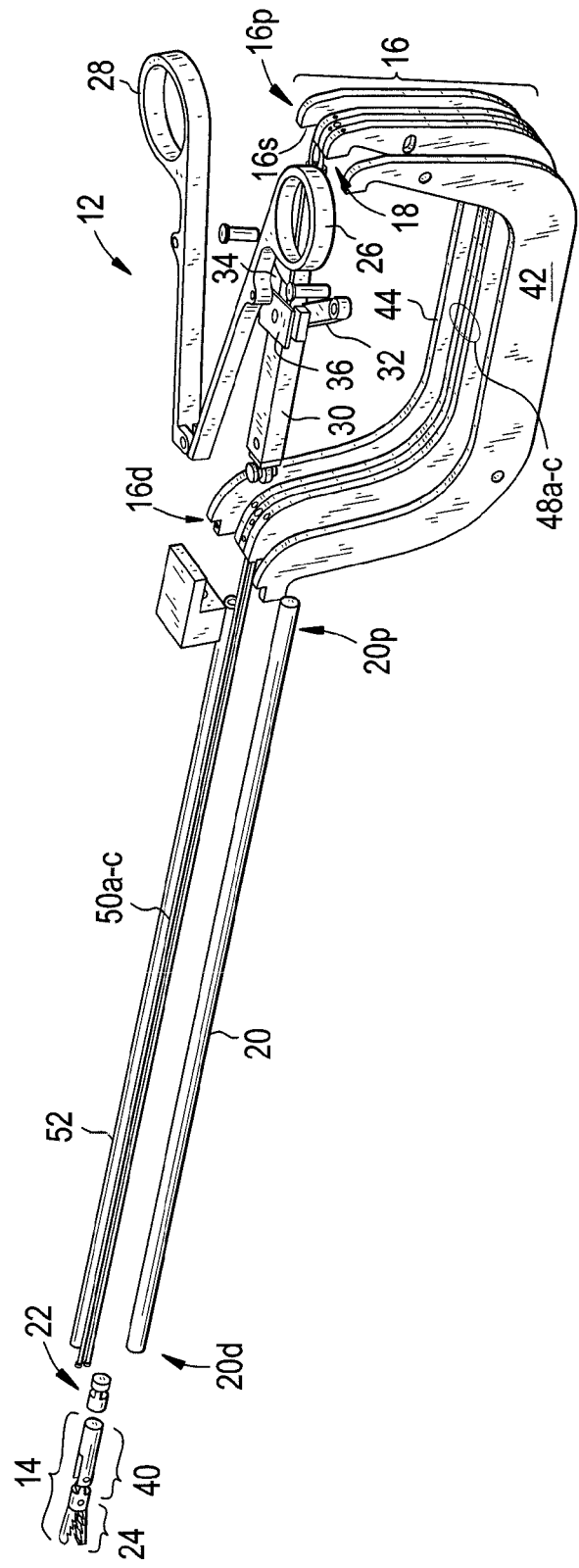
FIG. 1B is a perspective exploded view of the surgical device of FIG. 1A.

FIGS. 1A and 1B illustrate one exemplary embodiment of a laparoscopic device 10 that provides mimicking (not mirrored) motion between a handle or actuator 12 and an end effector assembly 14. As shown, the device 10 generally includes a frame 16 having proximal and distal ends 16p, 16d. The actuator 12 is movably coupled to the frame 16 by an input joint 18. The input joint 18 positioned distal to a distal-facing surface 16s of the proximal end 16p of the frame 16 such that the actuator 12 is positioned distal of the input joint 18 and extends distally from the proximal end 16p of the frame 16. The device 10 also includes an outer shaft 20 having a proximal end 20p coupled to the distal end 16d of the frame 16. An end effector assembly 14 is movably coupled to a distal end 20d of the outer shaft 20 by an output joint 22. In use, motion of the actuator 12 is transferred from the input joint 18 to the output joint 22, e.g., by a mechanical transmission, such that movement of the actuator 12 is mimicked by movement of the end effector assembly 14. The mimicking motion results from the location of the actuator 12 being distal, rather than proximal, to the input joint 18. Since both the actuator 12 and the end effector assembly 14 are distal to the input and output joints 18, 22, respectively, the end effector assembly 14 can identically mimic (in direction) the movement of the actuator 12. As indicated above, the motion can, however, differ in scale such that the motion of the actuator 12 is scaled up or down when transferred to the end effector assembly 14. The motion can include various types of movement, such as pitching (tilting forward and backward), yawing (turning left and right), rolling (tilting side to side), surging (moving forward and backward), heaving (moving up and down), swaying (moving left and right), and combinations thereof, as will be discussed in more detail below. A person skilled in the art will appreciate that, while a laparoscopic device is shown, the components can be used in a variety of other surgical devices, including endoscopic devices and other minimally invasive and open surgical devices. A person skilled in the art will also appreciate that the term "coupled," as used herein, is not limited to a direct connection between two components.

The actuator 12 can have a variety of configurations, and the particular configuration of the actuator 12 can depend on the particular configuration of the end effector assembly 14 since the actuator 12 is configured to allow mimicking motion by the end effector assembly 14. In the illustrated embodiment, the end effector assembly 14 includes an end effector in the form of opposed jaws 24, and thus the actuator 12 is in the form of a scissor-type actuator for opening and closing the opposed jaws 24. The actuator is thus configured to rest in the palm of a user's hand, and does not require attachment to a user's forearm/wrist. As a result, motion of the actuator relative to the input joint is independent of and does not correspond to motion of the user's hand relative to the user's wrist. Such a configuration is particularly advantageous as it allows the user to freely grasp and release the device during use, as may be desired. Such a configuration can also be advantageous as it does not require the user's forearm to be aligned with the axis of the elongate shaft. Rather, the user's forearm can extend at an angle transverse to the elongate shaft axis.

As best shown in FIGS. 1A and 1B, the actuator 12 generally includes first and second handles 26, 28 having distal ends 26d, 28d that are pivotally coupled to one another and to a distal end 30d of a central shaft 30. A first link 32 extends between the first handle 26 and a drive member 36 slidably disposed around and/or within the central shaft 30, and a second link 34 extends between the second handle 28 and the drive member 36. The first and second links 32, 34 are pivotally coupled to the first and second handles 26, 28, respectively, and to the drive member 36. Each handle can include a finger-loop or opening formed therein for receiving human digits, such as a thumb and a finger. When the handles 26, 28 are squeezed and moved toward the central shaft 30 to a closed position, the links 32, 34 pivot to push the drive member 36 distally relative to the central shaft 36. An actuation cable 38 can be coupled to the actuator 12 for transferring motion of the handles 26, 28 to the jaws 24 on the end effector assembly 14. While the actuation cable 38 can have a variety of configurations, in an exemplary embodiment the actuation cable 38 includes a flexible cable or sheath having an actuation wire (not shown) extending therethrough. The wire can be mated to the drive member 36. Distal (or forward) movement of the drive member 36 will therefore pull the wire in a distal direction, which will close the jaws 24 of the end effector assembly 14, as will be discussed in more detail below. Movement of the handles 26, 28 away from the central shaft 30 back to an open position will cause the links 32, 34 to move the drive member 36 proximally, thereby releasing the wire and allowing the jaws 24 to open. While not shown, a spring or other biasing mechanism can be coupled between the drive member 36 and a proximal portion of the central shaft 30 to bias the drive member 36 to the proximal position, thereby biasing the handles 26, 28 to the open position. Further details regarding the illustrated actuator are set forth in U.S. Pat. No. 5,951,574, which is hereby incorporated by reference in its entirety.

As further shown in FIGS. 1A and 1B, the illustrated end effector assembly 14 generally includes a clevis 40 having a generally hollow, elongate cylindrical configuration, and an end effector in the form of opposed jaws 24 pivotally coupled to a distal end of the clevis 40. The jaws 24 can be pivotally coupled to one another and to the clevis 40 at a location distal to a proximal end of each jaw 24. The actuation wire extending through the actuation cable 38 can be bifurcated at its distal end and a first terminal end of the actuation wire can connect to a proximal end of one of the jaws, and a second terminal end of the actuation wire can connect to a proximal end of the other jaw. As a result, proximal movement of the actuation wire will pull the proximal ends of the jaws 24 inward, thereby moving the jaws 24 to a closed position, as shown, and distal movement of the actuation wire will push the proximal ends of the jaws 24 outward, thereby moving the jaws 24 to an open position. Further details regarding the illustrated end effector assembly can be found, by way of non-limiting example, in U.S. Pat. No. 5,330,502 of Hassler et al., which is hereby incorporated by reference in its entirety. A person having ordinary skill in the art will appreciate that a variety of other actuators and end effectors can be used, including, for example, biopsy forceps for endoscopy and laparoscopic graspers.

Figure 2A:
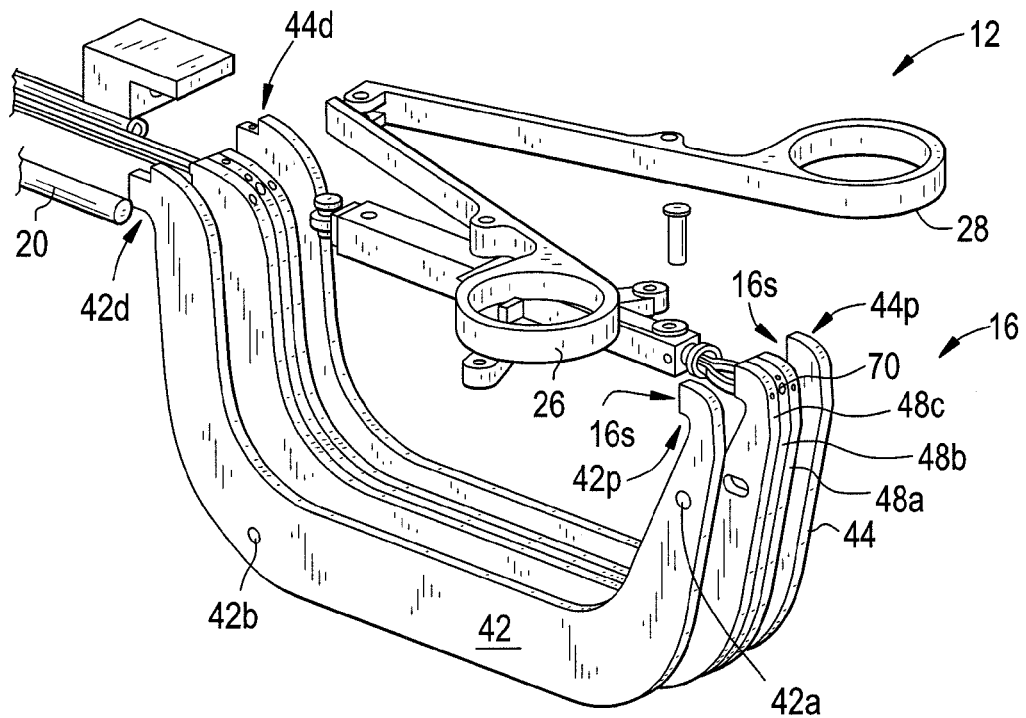
FIG. 2A is a top perspective exploded view of a proximal portion of the surgical device of FIG. 1A, showing an actuator, a frame, and a plurality of transmission plates.

The frame 16 is shown in more detail in FIG. 2A and generally includes two stationary plates 42, 44 that are substantially identical in shape and that are fixedly coupled to one another. Each stationary plate 42, 44 can have various shapes and sizes, but as shown the stationary plates 42, 44 are generally C-shaped. Such a configuration will allow the actuator 12 to extend distally from a proximal end 16p of the frame 16 and to extend coaxial with a longitudinal axis A of the outer shaft 20 when the end effector assembly 14 is in a resting or neutral position. The actuator 12 can, however, be offset from a longitudinal axis A of the outer shaft 20. Such offset positioning of the actuator 12 can be accommodated by calibrating the end effector assembly 14 and the actuator 12 at relative initial angles. For example, the initial position, or zero-point, of the actuator can be set to allow better operator hand position relative to the end effector. A person skill in the art will appreciate that the frame 16 can have a variety of other shapes and size to accommodate a desired positioning of the actuator 12.

Figure 3A:
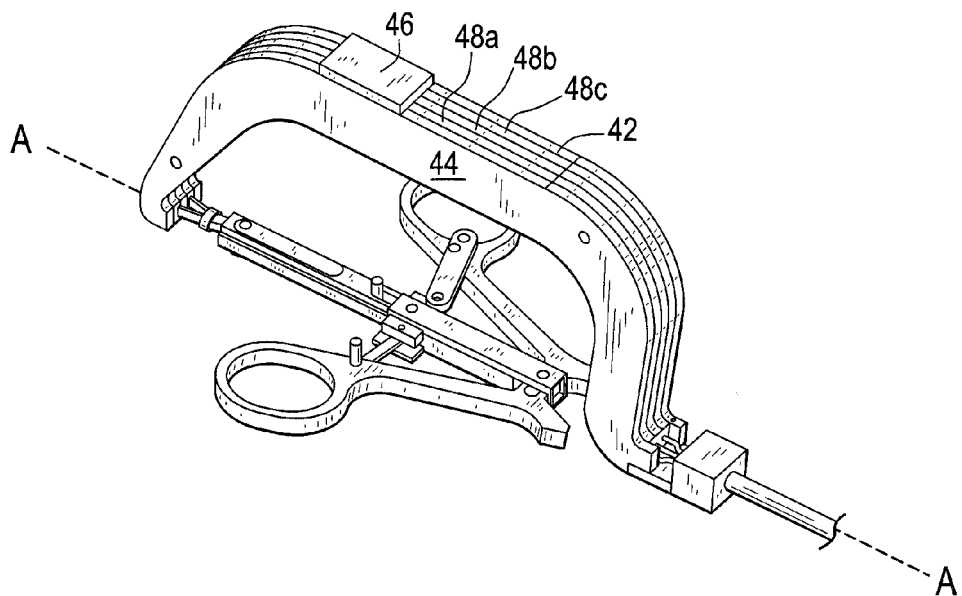
FIG. 3A is a bottom perspective view of the proximal portion of the device of FIG. 1A.

As further shown in FIG. 2A, the stationary plates 42, 44 can be fixedly coupled to one another by one or more pins, bolts, or other mating elements extending through the stationary plates 42, 44. For example, FIG. 2A illustrates a first hole 42a extending through a proximal portion of the first stationary plate 42 for receiving a first pin (not shown), and a second hole 42b extending through a distal portion of the first stationary plate 42 for receiving a second pin (not shown). The stationary plates 42, 44 can include any numbers or pins or other mating elements for rigidly and fixedly mating the plates 42, 44 such that movement between the first and second plates 42, 44 is prevented. In an exemplary embodiment, the stationary plates 42, 44 are held at a fixed distance apart from one another to allow a portion of the mechanical transmission to be disposed therebetween. As shown in FIGS. 1A and 3A, for example, the stationary plates 42, 44 can be held at a fixed distance apart using a strut of plate 46 that is mated to and extends between the stationary plates 42, 44.

As further shown in FIG. 2A, the proximal end 42p, 44p of the stationary plates 42, 44 can include a curved portion that extends distally to form a distal-facing surface 16s at the proximal end of the frame 16, and the distal end 42d, 44d of the stationary plates 42, 44 can similarly include a curved portion that extends distally to allow the distal end to couple to a proximal end 20p of the outer shaft 20, as will be discussed in more detail below.

Figure 2B:
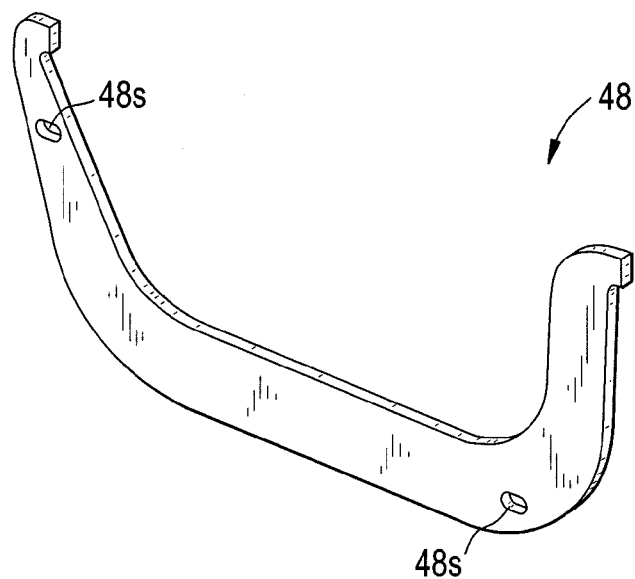
FIG. 2B is a perspective view of one of the transmission plates of FIG. 2A.

The mechanical transmission can also have a variety of configurations, but in the illustrated embodiment the mechanical transmission includes a plurality of transmission plates 48a, 48b, 48c and a plurality of transmission rods 50a, 50b, 50c. A person skilled in the art will appreciate that the mechanical transmission is not limited to plates and rods, and that other mechanical transmission components can be used to achieve the same effect. As shown in FIGS. 2A and 2B, each transmission plate 48a-c can have a shape and size that is substantially identical to the stationary plates 42, 44 that form the frame 16. The transmission plates 48a-c, however, can be movably disposed between the stationary plates 42, 44. In particular, each transmission plate 48a-c can be configured to slide relative to the stationary plates 42, 44. In an exemplary embodiment, the motion of the transmission plates 48a-c can be limited to sliding movement along a longitudinal axis that is the same as or parallel to the longitudinal axis A of the shaft 20. This can be achieved, for example, by forming longitudinally oriented slots 48s, shown in FIG. 2B, in the transmission plates for slidably receiving the pins that couple the stationary plates 42, 44. A person skilled in the art will appreciate that the plates can include slots or openings having other configurations configured to allow for movement of the plates in a desired direction. For example, where the actuator 12 is positioned offset or at an angle relative to the longitudinal axis A, the slots can be angled to accommodate such positioning. The transmission plates 48a-c can also or alternatively be captured between the stationary plates by one or more stop or support elements, such as the strut or plate 38 extending between the stationary plates 42, 44, as shown in FIGS. 1A and 3A.

Figure 3B:
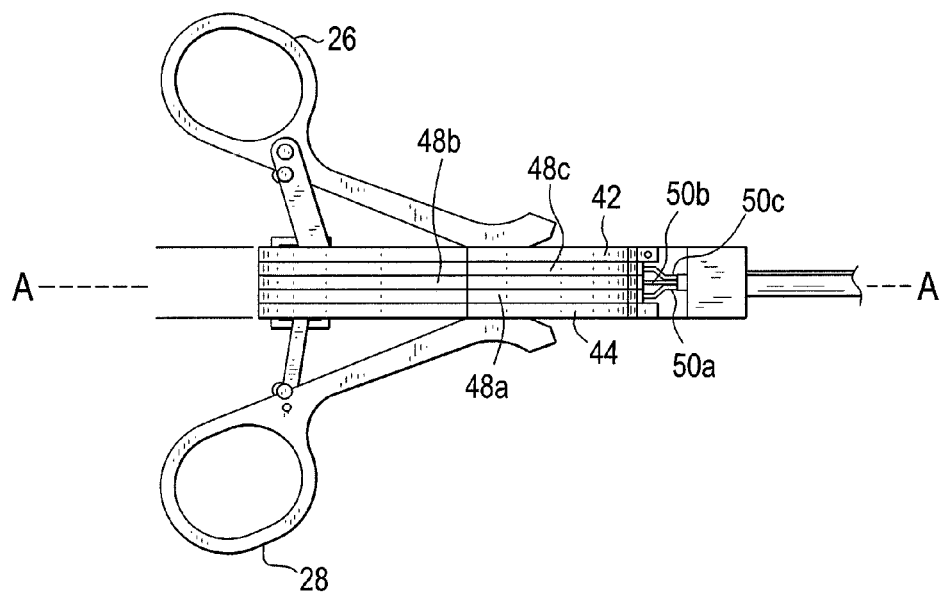
FIG. 3B is a bottom view of the proximal portion of the device of FIG. 1A.
Figure 3C:
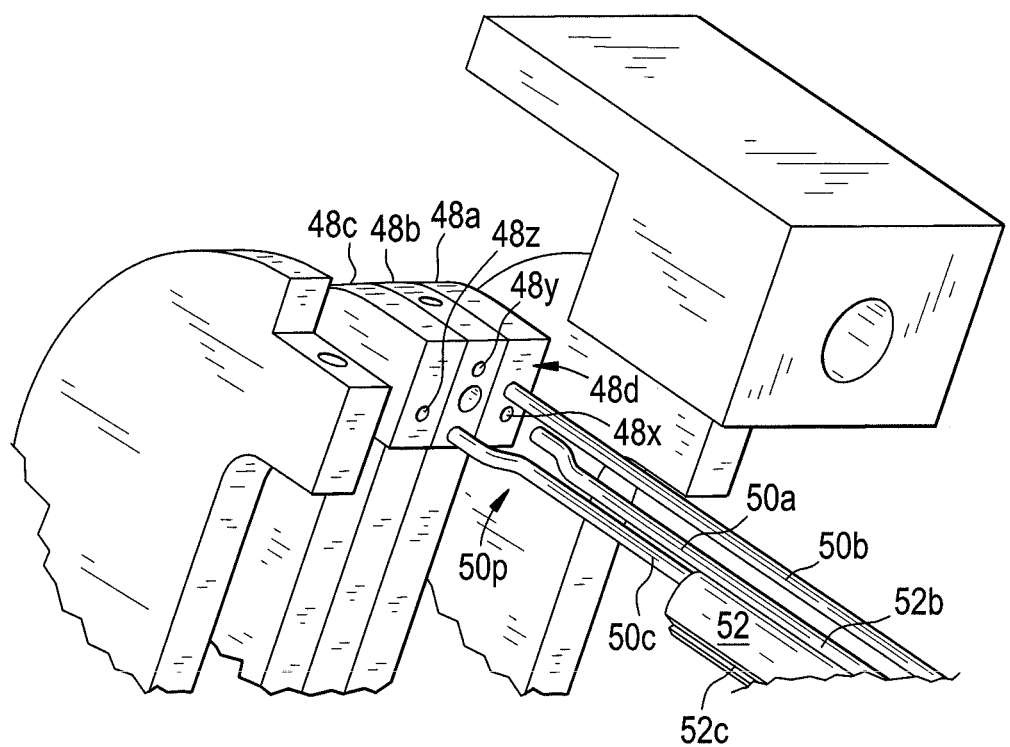
FIG. 3C is a perspective exploded view of a portion of the device of FIG. 1A showing the transmission rods and plates.

Each transmission plate 48a-c can be coupled to one of the transmission rods 50a-c to form a plate-rod assembly. One exemplary configuration for the transmission rods 50a-c is shown in FIGS. 3B-3C. As shown, the transmission rods 50a-c can be in the form of semi-rigid to rigid rods having a proximal end 50p that is fixedly connected to a distal-facing surface 48d of each transmission plate 48a-c. The transmission rods 50a-c can extend distally from the transmission plates 48a-c, through the outer shaft 20, and can have a distal end 50d (FIG. 5A) that is connected to the output joint 22, as discussed in detail below. The proximal and distal ends 50p, 50d of the transmission rods 50a-c can be fixedly connected to the plates 48a-c and movably coupled to the output joint 22, respectively, using various techniques known in the art. In the illustrated embodiment, the proximal terminal ends 50p of the rods 50a-c extend into and are immovably fixed within bore holes 48x, 48y, 48z formed in the distal-facing surface 48d of the distal end of the transmission plates 48a-c, as shown in FIG. 3C. The ends can be fixed to the plates using adhesives, by welding, or using various other fixation techniques. As a result of the fixed connection between the proximal ends 50p of the transmission rods 50a-c and the distal-facing surface 48d of the transmission plates 48a-c, the rods 50a-c essentially form an extension of the plates 48a-c and thereby move in coordination with the plates 48a-c. The distal terminal ends 50d of the rods 50a-c, on the other hand, are preferably movably coupled to the output joint 22, as will be discussed in more detail below with respect to FIGS. 5A-5C. In use, the rigidity of each transmission rod 50a-c can facilitate longitudinal motion of the transmission rods 50a-c through the outer shaft 20 in response to longitudinal motion of the transmission plates 48a-c relative to the stationary plates 42, 44. Each plate-rod assembly can be effective to transfer a specific type of motion from the actuator 12 to the end effector assembly 14, as discussed further below.

As further shown in FIG. 3C, as well as FIG. 1B, while the transmission rods 50a-c extend through the outer shaft 20, the transmission rods 50a-c can also extend through an inner shaft 52 disposed within the outer shaft 20. In particular, the inner shaft 52 can include three outer channels (only two channels 52b and 52c are shown) formed therein and extending longitudinally along the length thereof for slidably seating the transmission rods 50a-c. The outer channels can be positioned to correspond to the positioning of the transmission rods 50a-c, as well be discussed in more detail below, and the channels can be configured to maintain such positioning of the transmission rods 50a-c. The inner shaft 52 can be freely movably disposed within the outer shaft 20 such that the inner shaft 52 can rotate with the transmission rods 50a-c relative to the outer shaft 20, as will also be discussed in more detail below.

As indicated above, the mechanical transmission can be coupled between an input joint 18 and an output joint 22. The input joint 18 can be fixedly and rigidly coupled to the actuator 12, and it can be movably coupled to the proximal end 48p of the transmission plates 48a-c. The output joint 22 similarly can be fixedly and rigidly coupled to the end effector assembly 14, and it can movably couple to the distal end 50d of the transmission rods 50a-c. The input and output joints 18, 22 can have various configurations, but each joint is preferably configured to allow motion of the actuator 12 to be transferred through the mechanical transmission to cause mimicking motion of the end effector assembly 14. In an exemplary embodiment, the input and output joints 18, 22 are in the form of wrists that pivot in response to motion of the mechanical transmission. In an exemplary embodiment, each wrist includes a plurality of sockets formed therein for movably seating a ball. The number of sockets can correspond to the number of plate-rod assemblies used in the mechanical transmission. In use, the wrists can allow the actuator 12 and end effector assembly 14 to have one or more degrees of freedom, including pitching (tilting forward and backward), yawing (turning left and right), rolling (tilting side to side), surging (moving forward and backward), heaving (moving up and down), swaying (moving left and right), and combinations thereof.

Figure 4A:
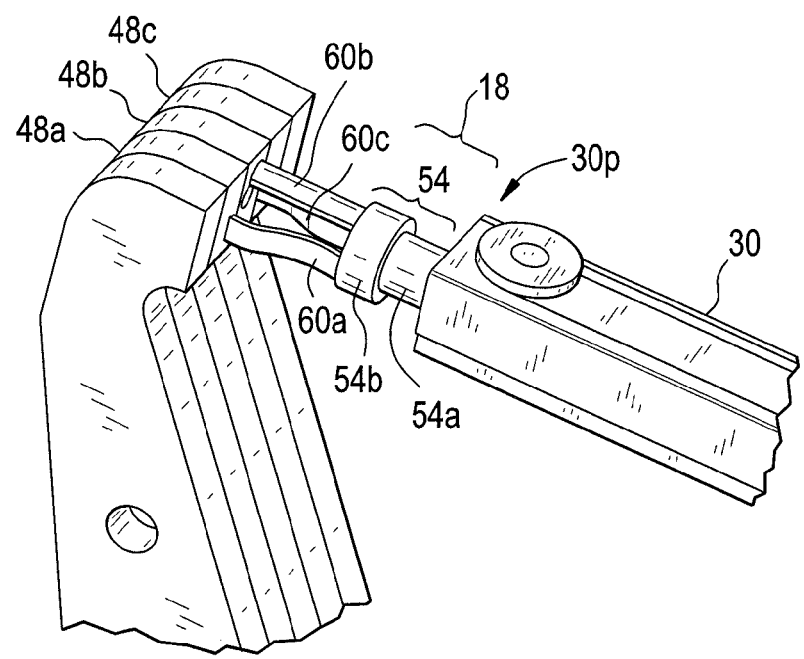
FIG. 4A is an enlarged perspective view of an input joint of the device of FIG. 1A.
Figure 4B:
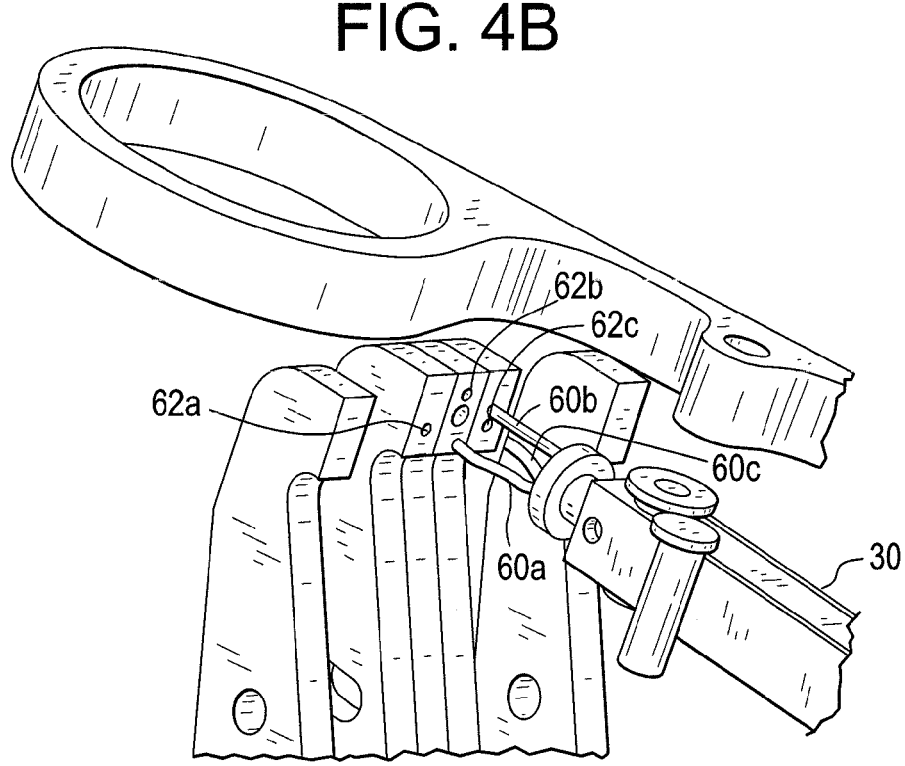
FIG. 4B is an exploded perspective view of the input joint of FIG. 4A.

FIGS. 4A-4B illustrate one exemplary configuration for an input joint 18. As illustrated, the wrist that forms the input joint 18 is in the form of a housing 54 that is fixedly coupled to a proximal-facing surface of a proximal end 30*p* of the central shaft 30 of the actuator 12. The illustrated housing 54 can include a cylindrical portion 54*a* and a collar 54*b* disposed around the cylindrical portion 54*a*. The particular configuration of the cylindrical portion 54*a* and the collar 54*b* will be discussed in more detail below with respect to the output joint 22. In general, a distal end of the cylindrical portion 54*a* can extend into a corresponding lumen (not shown) formed in the central shaft 30 of the actuator 12, and a proximal end of the cylindrical portion 54*a* and the collar 54*b* can couple to the mechanical transmission. In particular, when the collar 54*b* is disposed around the cylindrical portion 54*a*, the collar 54*b* and cylindrical portion 54*a* will form sockets, discussed further below. Each socket is configured to trap and movably seat a ball end (not shown) formed on a proximal end of a connecting rod 60*a*, 60*b*, 60*c* for movably mating the input joint 18 to the transmission pates 48*a-c*. Each connecting rod 60*a-c* can have a generally rigid or semi-rigid configuration, with a proximal end that extends into and fixedly mates with a bore hole 62*a*, 62*b*, 62*c* formed in the distal-facing surface of the proximal end 48*b* of a transmission plate 48*a-c* to thereby mate the actuator 12 to the transmission plates 48*a-c*. The components can be fixedly mated to one another using various techniques known in the art, such as welding or with adhesives.

Figure 5B:
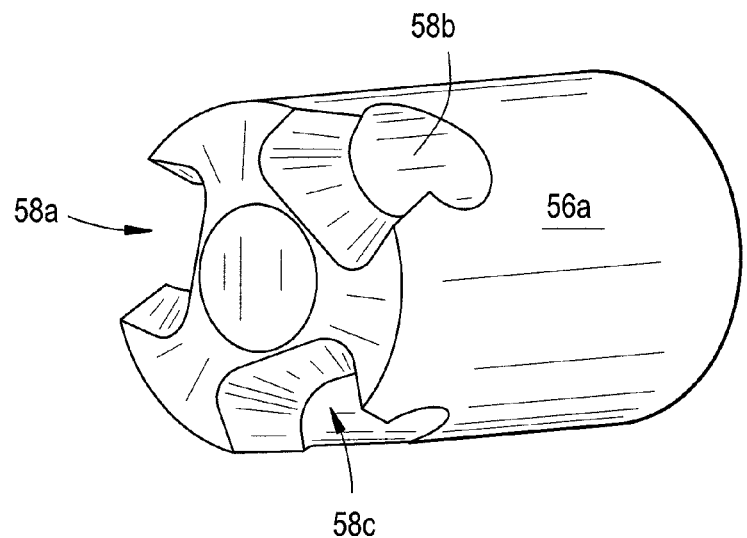
FIG. 5B is a perspective view of a housing of the output joint of FIG. 5A.

FIGS. 5A-5B illustrate one exemplary configuration for an output joint 22, which can be similar to the input joint. As illustrated, the wrist that forms the output joint 22 is in the form of a housing 56 that is fixedly coupled to a proximal end 14*p* of the end effector assembly 14. The illustrated housing 54 includes a cylindrical portion 56*a* and a collar 56*b* disposed around the cylindrical portion 54*b*. As shown in FIG. 5B, the cylindrical portion 56*a* has three cut-outs 58*a*, 58*b*, 58*c* formed in an external surface thereof adjacent to a terminal end thereof for seating ball ends on the transmission rods 50*a-c*. The cut-outs 58*a-c* can be spaced equidistant around a perimeter of the cylindrical. The collar 56*b*, shown in FIG. 5C, can similarly include three cut-outs 64*a*, 64*b*, 64*c* formed in an inner surface thereof that align with the cut-outs 58*a-c* formed in the cylindrical portion 56*a*. As a result, when the collar 56*b* is disposed around the cylindrical portion 56*a*, the cut-outs in the collar 56*b* and cylindrical portion 56*a* will form the sockets that trap the ball ends of the transmission rods 50*a-c* therein. The opposite end of the cylindrical portion 56*a* for the output joint 22 can be inserted into a corresponding lumen 141 formed in the end effector assembly 14. The components can be fixedly mated to one another using various techniques known in the art, such as welding or with adhesives.

Figure 5C:
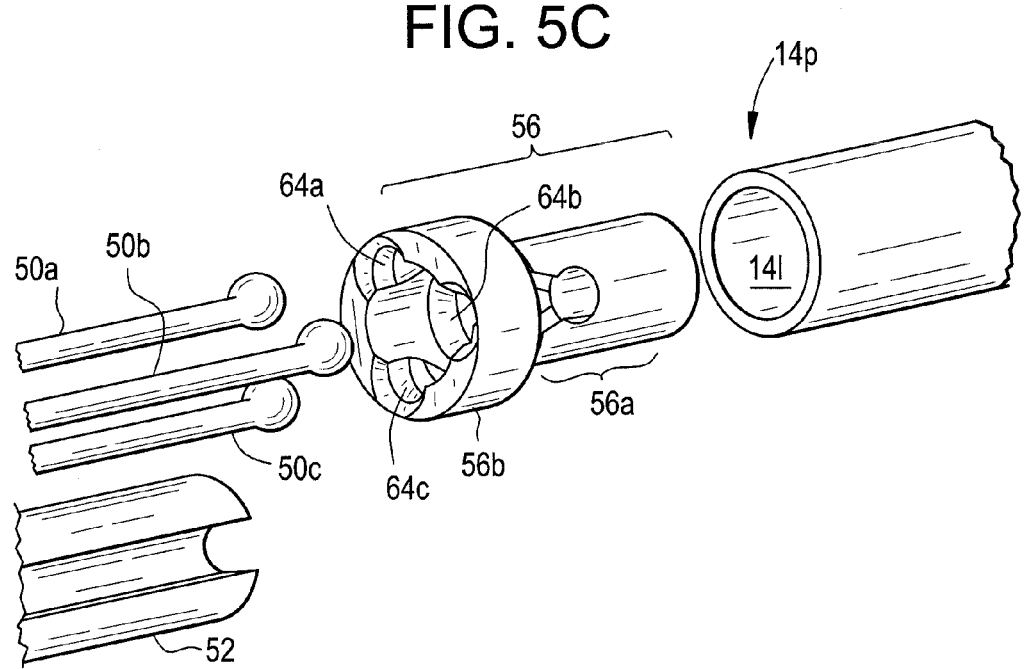
FIG. 5C is an exploded perspective view of the output joint of FIG. 5A.

In use, each plate-rod assembly can transfer a predetermined motion from the input joint 18 to the output joint 22. The predetermined motion caused by each plate-rod assembly can be determined by the location of the ball-and-socket joint within the input and output joints 18, 22. For example, as best shown in FIG. 4B, the connecting rods 60*a-c*, which extend from the sockets in the input joint 18, can have a triangular configuration around the central axis A. As a result, a first connecting rod 60*a* (and thus a first socket, not shown) will be positioned inferior and laterally offset, e.g., to the right, of the central axis A, a second connecting rod 60*b* (and thus a second socket, not shown) will be positioned superior to the central axis A, and a third connecting rod 60*c* (and thus a third socket, not shown) will be positioned inferior and laterally offset, e.g., to the left, of the central axis A. The output joint 22 can have the same positioning of sockets 64*a-c*, as shown in FIG. 5C. As a result, each transmission plate-rod assembly will transfer a predetermined motion from the input joint 18 to the output joint 22. In particular, since connecting rod 60*b* is positioned superior to the axis A, connecting rod 60*b* will transfer pitch (up/down) of the actuator 12 to the end effector assembly 14, and since connecting rods 60*a* and 60*c* are positioned inferior and laterally outward relative to the axis A, connecting rods 60*a* and 60*c* will transfer yaw (left/right) of the actuator 12 to the end effector assembly 14. Such movements are illustrated and discussed in more detail with respect to FIGS. 6A and 6B. A person skilled in the art will appreciate that the mechanical transmission can include any number of plate-rod assemblies, and additional plate-rod assemblies may provide additional freedom of movement and control over such movement. For example, in another embodiment the mechanical transmission can include four plates and four rods, and the rods can be positioned equidistant around a circumference of the input and output joints 18, 22. As such, two of the rods on opposite sides of the joint can provide pitch and the other two rods can provide yaw. In other embodiments, the mechanical transmission can include five or six plate-rod assemblies.

Figure 6A:
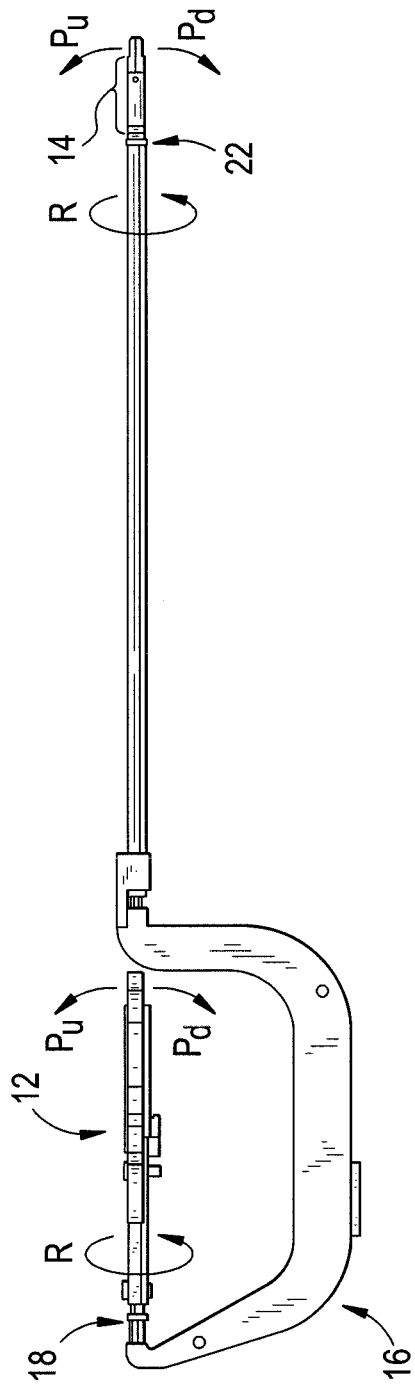
FIG. 6A is a side view of the device of FIG. 1A.

Referring first to FIG. 6A, pivotal movement of the actuator 12, and thus the input joint 18, in an upward direction $P_u$ will push the superior positioned connecting rod 60*b* proximally, thereby pushing transmission plate 48*b* proximally. Proximal movement of transmission plate 48*b* will cause corresponding proximal movement of transmission rod 50*b*, which in turn will pivot within the socket 64*b* in the housing 56 to pull on the top of the output joint 22 causing the output joint 22, and thus the end effector assembly 14 mated thereto, to pivot in the same direction as the actuator 12, i.e., in an upward direction $P_u$. Conversely, pivotal movement of the actuator 12, and thus the input joint 18, in a downward direction $P_d$ will pull connecting rod 60*b* distally, thereby pulling the first transmission plate 48*b* distally. Distal movement of transmission plate 48*b* will cause corresponding distal movement of transmission rod 50*b*, which in turn will push on the top of the output joint 22 causing the output joint 22, and thus the end effector assembly 14 mated thereto, to pivot in the same direction as the actuator 12, i.e., in a downward direction $P_d$.

Figure 6B:
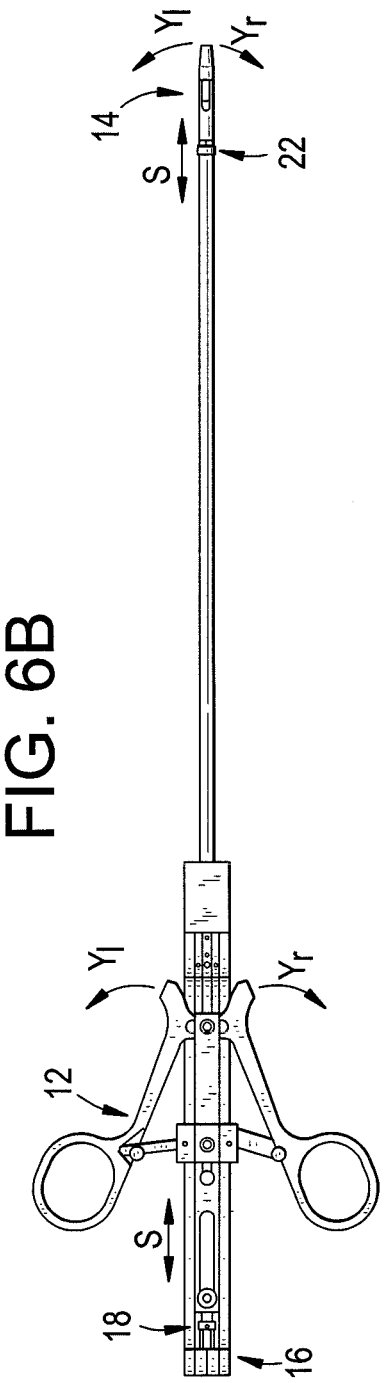
FIG. 6B is a top view of the device of FIG. 1A.

Referring to FIG. 6B, pivotal movement of the actuator 12, and thus the input joint 18, in a leftward direction. $Y_1$ will push connecting rod 60*c* proximally while pulling connecting rod 60*a* distally. As a result, transmission plate 48*c* is pushed proximally by connecting rod 60*c* and transmission plate 48*a* is pulled distally by connecting rod 60*a*. Proximal movement of transmission plate 48*c* and distal movement of transmission plate 48*a* will cause corresponding proximal movement of transmission rod 50*c* and distal movement of transmission rod 50*a*, which in turn will cause the rods 50*c*, 50*c* to pivot within the sockets 64*c*, 64*a* in the housing 56 and will to pull on the left side of the output joint 22 and push on the right side of the output joint 22 causing the output joint 22, and thus the end effector assembly 14 mated thereto, to pivot in the same direction as the actuator 12, i.e., in a leftward direction $Y_l$. Conversely, pivotal movement of the actuator 12, and thus the input joint 18; in a rightward direction $Y_r$, will pull connecting rod 60a distally while pushing connecting rod 60c proximally. As a result, transmission plate 48a is pulled distally by connecting rod 60a and transmission plate 48c is pushed proximally by connecting rod 60c. Distal movement of transmission plate 48c and proximal movement of transmission plate 48a will cause corresponding distal movement of transmission rod 50a and proximal movement of transmission rod 50c, which in turn will push on the left side of the output joint 22 and pull on the right side of the output joint 22 causing the output joint 22, and thus the end effector assembly 14 mated thereto, to move in the same direction as the actuator 12, i.e., to pivot in a rightward direction $Y_r$.

Figure 7:
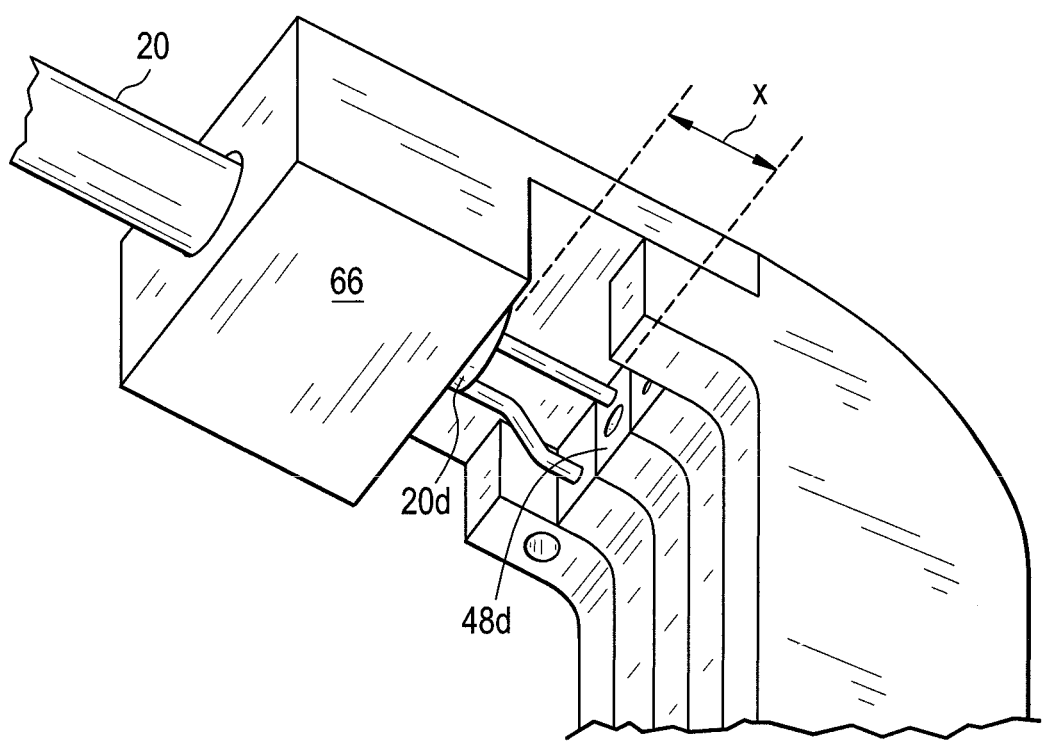
FIG. 7 is a perspective view of the proximal portion of the device of FIG. 1A.

The device can also be configured to transfer surging of the actuator 12 to the end effector assembly 14. In particular, movement of the actuator 12 in a direction indicated by the arrow labeled S in FIG. 6B can simultaneously move all three plate-rod assemblies in forward and backward directions relative to the frame 16 and the outer shaft 20. As a result of such movement, the end effector assembly 14 will surge in coordination with the actuator 12, i.e., the end effector assembly 14 will move forward and backward relative to the outer shaft 20 and frame thereby mimicking the motion of the actuator 12. While various techniques can be used to allow for surging of the actuator 12, and thus the end effector assembly 14, in one embodiment the outer shaft 20 can have a length that is less than the length of the transmission rods 50a-c, as measured from the distal-facing surface at the distal end 48d of the transmission plates 48a-c to the proximal end 14p of the end effector assembly 14. The difference in length can provide a gap between one end of the outer shaft 20 and the clevis 40 on the end effector assembly 14. This is illustrated in FIG. 7, which shows the proximal end 20p of the outer shaft 20 being spaced a distance X apart from the distal-facing surface 48d of the transmission plates 48a-c. While not shown, the distal end 20d of the outer shaft 20 can abut, but be free from attachment to, the proximal end 14p of the clevis 40 on the end effector assembly 14. The outer shaft 20 can, however, be fixedly coupled to the clevis 40 by a joining element, such as the L-shaped block 66 shown in FIG. 7. As a result, the outer shaft 20 will remain fixed relative to the frame 16, thus allowing the entire mechanical transmission to surge (move forward and backward) relative to the frame 16. In particular, when the actuator 12 is moved forward or distally relative to the frame 16, the actuator 12 will move all three plate-rod assemblies in a distal direction relative to the frame 16 and the outer shaft 20, which is fixed to the frame 16. The inner shaft 52 can also move with the transmission rods 50a-c. As a result of such movement, the end effector assembly 14 will move distally thereby closing or eliminating the gap between the proximal end 20p of the shaft 20 and the transmission plates 48a-c, and forming or increasing a gap between the distal end 20d of the outer shaft 20 and the end effector assembly 14. Conversely, movement of the actuator 12 in a backward or proximal direction relative to the frame 16 will move all three plate-rod assemblies in a proximal direction relative to the frame 16 and the outer shaft 20. As a result, the end effector assembly 14 will move proximally thereby creating or increasing the gap between the proximal end 20p of the shaft 20 and the transmission plates 48a-c, and closing or eliminating the gap between the distal end 20d of the outer shaft 20 and the end effector assembly 14.

A person skilled in the art will appreciate that, while the illustrated mechanical transmission and input and output joints 18, 22 provide for four degrees of freedom (pitch, yaw, roll, and surge), the actuator 12 and end effector assembly 14 are polyaxially movable, and thus the motion can include any combination of pitch, yaw, roll, and surge. Moreover, the mechanical transmission and input and output joints 18, 22 can be configured to provide for any number and any combination of degrees of freedom. For example, additional degrees of freedom, such as heave (translation of the entire end effector assembly 14 upward and downward) and sway (translation of the entire end effector assembly 14 in left and right directions), can be provided through additional plate-rod assemblies and/or through additional joints.

The mechanical transmission, and/or input and output joints 18, 22 can also be configured to allow for motion scaling, i.e., the motion of the actuator 12 is increased or decreased when transferred to the end effector assembly 14. For example, in one embodiment, the sockets 64a-c between the transmission rods 50a-c and the housing 56 at the output joint 22 can be positioned a distance radially outward from the longitudinal axis A that is greater then a distance between the longitudinal axis and the socket on the input joint 18, thereby scaling down the motion of the end effector assembly 14 relative to the actuator 12. As a result, large movement of the actuator 12 will result in smaller movement of the end effector assembly 14.

As previously explained, the device 10 can also include an actuation cable 38 extending from the actuator 12, through the frame 16 and the outer shaft 20, and coupling to the end effector assembly 14 to actuate the end effector, e.g., open/close, fire, etc. The actuation cable 38 need not be part of the mechanical transmission, and instead can merely extend through one of more lumens formed in the frame 16 and the outer shaft 20. In particular, the housing 54 of the input joint 18 can include a central lumen (not shown) extending therethrough for receiving the actuation cable 38, which is coupled to the actuator 12. The cable 38 can extend out through the lumen in the input joint 18 and can extend through a central hole 68 (FIG. 4B) formed in the proximal end of the second transmission plate 48b. This will allow the cable 38 to extend around an exterior portion of the frame 16, as shown in FIG. 1A. The cable 38 can then extend into a hole 70 (FIG. 2A) formed in a distal end of the second transmission plate 48b and can extend through the outer shaft 20. In an exemplary embodiment, the inner shaft 52 has a central lumen formed therein for receiving the actuation cable 38. Alternatively, one of the channels in the inner shaft 52 can be configured to seat both a transmission rod 48a-c and the actuation cable 38. The distal end of the actuation cable 38 can be coupled to the end effector 14, as previously explained.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. By way of non-limiting example, the end effector assembly 14 can be removed, cleaned, sterilized, and reused. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a frame having proximal and distal ends;
   an elongate shaft extending distally from the distal end of the frame;
   a mechanical transmission extending through the frame and elongate shaft, the transmission extending between an input joint at the proximal end of the frame and an output joint at a distal end of the elongate shaft, the transmission including at least one transmission plate disposed in the frame and slidably movable along a longitudinal axis of the device relative to the frame;
   an actuator extending distally from the proximal end of the frame, the actuator being coupled to the input joint and being polyaxially movable relative to the frame; and
   an end effector assembly positioned distal of the distal end of the elongate shaft, the end effector assembly being coupled to the output joint;
   wherein motion of the input joint is effective to cause correlating motion of the output joint such that movement of the actuator is mimicked by movement of the end effector assembly.

2. The surgical device of claim 1, wherein the output joint comprises a ball-and-socket connection formed between the mechanical transmission and the end effector assembly.

3. The surgical device of claim 1, wherein the input joint comprises a ball-and-socket connection formed between the mechanical transmission and the actuator.

4. The surgical device of claim 1, wherein the mechanical transmission comprises at least one transmission rod having a distal end connected to the output joint and a proximal end connected to at least one transmission plate slidably disposed in the frame, the at least one transmission plate having a proximal end coupled to the input joint.

5. The surgical device of claim 4, wherein the proximal end of the at least one transmission plate is coupled to the input joint by a coupler rod extending from the at least one transmission plate.

6. The surgical device of claim 4, wherein the at least one transmission rod and the at least one transmission plate comprises a first transmission rod connected to a first transmission plate, a second transmission rod connected to a second transmission plate, and a third transmission rod connected to a third transmission plate, the first, second, and third transmission rods and plates being configured to cause polyaxial articulation of the end effector assembly relative to the elongate shaft.

7. The surgical device of claim 4, wherein movement of the actuator is effective to cause translation of the at least one transmission plate, and wherein translation of the at least one transmission plate is effective to cause translation of the at least one transmission rod coupled to the at least one transmission plate.

8. The surgical device of claim 1, wherein the actuator and the end effector assembly each have at least four degrees of freedom.

9. The surgical device of claim 8, wherein the at least four degrees of freedom are selected from the group consisting of surging, heaving, swaying, yawing, pitching, and rolling.

10. The surgical device of claim 1, wherein the actuator and the end effector assembly are configured to surge relative to the elongate shaft.

11. The surgical device of claim 1, further comprising an actuation wire coupled between the actuator and the end effector assembly and configured to transfer opening and closing motion of the actuator to opening and closing motion of an end effector on the end effector assembly.

12. The surgical device of claim 1, wherein the frame is C-shaped.

13. The surgical device of claim 1, wherein the movement of the end effector assembly is different in scale than the movement of the actuator.

14. A surgical device, comprising:
   a frame having proximal and distal ends;
   a hand-held actuator extending distally from a distal-facing surface of a proximal end of the frame and having at least four degrees of freedom relative to the frame, the actuator being configured to be grasped by a user's hand without attaching to the user's wrist;
   an elongate shaft extending distally from the distal end of the frame and having an end effector assembly movably coupled to a distal end thereof; and
   a mechanical transmission extending through the frame and the elongate shaft, the mechanical transmission being operably coupled between the actuator and the end effector assembly such that the mechanical transmission transfers motion of the actuator to cause mimicking motion of the end effector assembly,
   wherein the at least four degrees of freedom include at least one of rolling about a longitudinal axis of the device and surging along the longitudinal axis.

15. The surgical device of claim 14, wherein the hand-held actuator comprises a scissor-type actuator.

16. The surgical device of claim 14, wherein the frame is substantially C-shaped and the actuator is positioned between proximal and distal ends of the frame.

17. The surgical device of claim 14, wherein the mechanical transmission comprises at least one transmission plate slidably disposed within the frame and at least one transmission rod connected to the transmission plate and slidably disposed through the elongate shaft.

18. The surgical device of claim 14, wherein the frame comprises first and second stationary plates coupled to one another, and wherein the mechanical transmission extends between the first and second stationary plates.

19. The surgical device of claim 14, wherein the mechanical transmission comprises:
   a first transmission plate disposed in the frame and a first transmission rod connected to the first transmission plate and extending through the elongate shaft;
   a second transmission plate disposed in the frame and a second transmission rod connected to the second transmission plate and extending through the elongate shaft; and
   a third transmission plate disposed in the frame and a third transmission rod connected to the third transmission plate and extending through the elongate shaft.

20. The surgical device of claim 19, wherein the first, second, and third transmission plates and rods are effective to cause polyaxial articulation of the end effector assembly relative to a longitudinal axis of the elongate shaft.

21. The surgical device of claim 14, wherein the elongate shaft includes an outer tube spaced a distance apart from at least one of the distal end of the frame and a proximal end of the end effector assembly.

22. The surgical device of claim 14, further comprising an input joint disposed between the actuator and a proximal end of the mechanical transmission, and an output joint disposed between a distal end of the mechanical transmission and the end effector assembly.

23. The surgical device of claim 14, wherein the actuator and the end effector assembly are coaxially aligned when the actuator and the end effector assembly are in a resting position.

24. A surgical device, comprising:
   a frame having proximal and distal ends;
   an elongate shaft extending distally from the distal end of the frame;
   a mechanical transmission extending through the frame and elongate shaft, the transmission extending between an input joint at the proximal end of the frame and an output joint at a distal end of the elongate shaft;
   an actuator extending distally from the proximal end of the frame, the actuator being coupled to the input joint; and
   an end effector assembly positioned distal of the distal end of the elongate shaft, the end effector assembly being coupled to the output joint;
   wherein motion of the input joint is effective to cause correlating motion of the output joint such that movement of the actuator is mimicked by movement of the end effector assembly, and wherein at least one of the input joint and the output joint comprises a ball-and-socket connection.

* * * * *